United States Patent
Moradi et al.

(10) Patent No.: US 10,807,955 B2
(45) Date of Patent: Oct. 20, 2020

(54) PROCESS FOR THE PREPARATION OF A 2-PYRIDYLETHYLCARBOXAMIDE DERIVATIVE

(71) Applicant: Bayer CropScience Aktiengesellschaft, Monheim am Rhein (DE)

(72) Inventors: Wahed Ahmed Moradi, Monheim (DE); Albert Schnatterer, Leverkusen (DE); Dietmar Bielefeldt, Ratingen (DE); Rolf Gertzmann, Leverkusen (DE); Dirk Havekost, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/471,132

(22) PCT Filed: Dec. 12, 2017

(86) PCT No.: PCT/EP2017/082442
§ 371 (c)(1),
(2) Date: Jun. 19, 2019

(87) PCT Pub. No.: WO2018/114484
PCT Pub. Date: Jun. 28, 2018

(65) Prior Publication Data
US 2020/0039937 A1   Feb. 6, 2020

(30) Foreign Application Priority Data
Dec. 21, 2016 (EP) .................................. 16205583

(51) Int. Cl.
*C07D 213/61* (2006.01)
(52) U.S. Cl.
CPC ................... *C07D 213/61* (2013.01)

(58) Field of Classification Search
CPC .................................................. C07D 213/61
See application file for complete search history.

(56) References Cited

U.S. PATENT DOCUMENTS

| 7,572,818 B2 | 8/2009 | Mansfield et al. |
| 7,790,901 B2 | 9/2010 | Lhermitte et al. |
| 8,865,908 B2 | 10/2014 | Lhermitte et al. |
| 9,301,526 B2 | 4/2016 | Greul et al. |
| 2008/0086008 A1 | 4/2008 | Lhermitte et al. |
| 2010/0292485 A1 | 11/2010 | Lhermitte et al. |
| 2014/0249149 A1 | 9/2014 | Greul et al. |

FOREIGN PATENT DOCUMENTS

| WO | 2004016088 A2 | 2/2004 |
| WO | 2006067103 A2 | 6/2006 |
| WO | 2013064460 A1 | 5/2013 |

OTHER PUBLICATIONS

International Search Report for PCT/EP2017/082442, dated Mar. 5, 2018.
Extended European Search Report Issued in EP16205583 dated Apr. 7, 2017.

*Primary Examiner* — John M Mauro
(74) *Attorney, Agent, or Firm* — McBee Moore & Vanik IP, LLC

(57) ABSTRACT

Described is a process for the preparation of a N-[2-(2-pyridinyl)ethyl]carboxamide derivative of general formula (I) or a salt thereof.

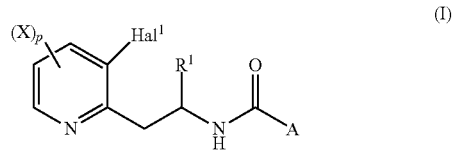

15 Claims, No Drawings

PROCESS FOR THE PREPARATION OF A 2-PYRIDYLETHYLCARBOXAMIDE DERIVATIVE

CROSS-REFERENCE TO RELATED APPLICATIONS

This application is the National Stage entry of International Application No. PCT/EP2017/082442, filed 12 Dec. 2017, which claims priority to European Patent Application No. 16205583.4, filed 21 Dec. 2016.

BACKGROUND

Field

The present invention relates to a novel process for the preparation of N-[2-(2-pyridinyl)ethyl]carboxamide derivative which is useful as pesticide compound, starting with a halogenobenzoyl derivative to produce a N-acetoxymethylcarboxamide derivative and then coupling it with a 2-pyridyl acetate derivative.

Description of Related Art

Patent application WO 2004/016088 discloses the preparation of N-[2-(2-pyridinyl)ethyl]benzamide derivatives starting from 2-halogenopyridine derivatives to produce 2-ethylaminopyridine derivatives and then coupling these 2-ethylaminopyridine derivatives with a halogenobenzoyl derivative.

Patent application WO2006/067103 discloses the preparation of N-[2-(2-pyridinyl)ethyl]benzamide derivatives starting from a halogenobenzoyl derivative to produce a N-acetoxymethylcarboxamide derivative and then coupling it with a 2-pyridyl acetate derivative. The preparation of malonic ester derivatives from halogeno-pyridyl derivatives requires very polar solvents. The resulting water in the reaction may lead to formation of several side components like hydroxy-pyridyl derivatives, alkoxy-pyridyl derivatives, or N-dimethylamino pyridyl derivatives, thereby affecting selectivity of the reaction and overall yield. In addition, in an industrial scale production process there is a need to remove the resulting water. This may require an additional step in the production or additional efforts in order to remove the water, thereby further increasing costs and affecting yield.

Secondly, saponification refers to the process of the hydrolysis of an ester in the presence of an aqueous solution of hydroxide. If the ester is not or only in small amounts soluble in water, this would lead to a low rate of conversion for the ester as the aqueous solution of hydroxide is forming with the non-water soluble ester optionally in the presence of a solvent a two-phase system. Therefore there is the need to search for other option enabling a quicker and more efficient reaction of the aqueous solution of hydroxide with a non-water soluble ester.

SUMMARY

We have now found an alternative method to prepare N-[2-(2-pyridinyl)ethyl]carboxamide derivative which overcomes these problems and which is applicable to industrial scale operation.

Accordingly, the present invention relates to a process for the preparation of a N-[2-(2-pyridinyl)ethyl]carboxamide derivative of general formula (I) or a salt thereof

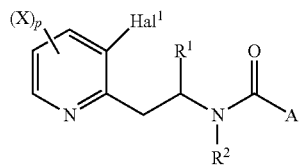

in which:
p is an integer equal to 1, 2, or 3;
X is the same or different and is a hydrogen atom, a halogen atom, a $C_1$-$C_8$-alkyl, a $C_1$-$C_8$-halogenoalkyl having 1 to 5 halogen atoms;
$R^1$ is a hydrogen atom, a $C_1$-$C_8$-alkyl, a $C_1$-$C_8$-halogenoalkyl having 1 to 5 halogen atoms or a $C_1$-$C_8$-alkoxycarbonyl;
$R^2$ is a hydrogen atom or a cyclopropyl group;
$Hal^1$ represents a halogen atom;
and
A represents a phenyl group being optionally substituted by one or more substituents chosen independently of each other as being a halogen atom, a $C_1$-$C_8$-alkyl, a $C_1$-$C_8$-halogenoalkyl having 1 to 5 halogen atoms;
as to the N-oxides of the 2-pyridine thereof;
said process comprising:
(A)—a first step according to reaction scheme 1:

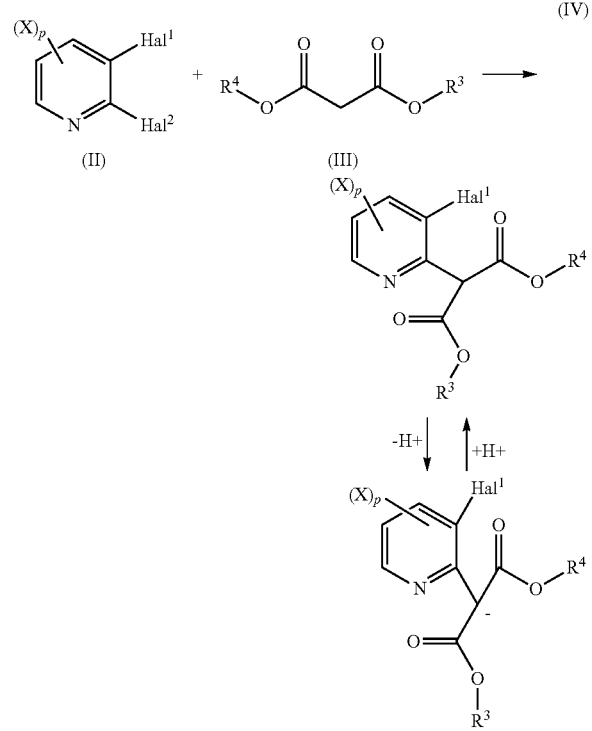

in which:
A and $R^2$ are as defined above;
X and p are defined as above; and
$Hal^1$ or $Hal^2$ represent independently from each other a halogen atom;
$R^3$ and $R^4$ represent independently from each other a $C_1$-$C_6$-alkyl;

3 comprising the reaction of a halogenopyridyl derivative of formula (II) with a malonic dialkyl ester of formula (III) in the presence of a base and a polar solvent to provide a malonic dialkyl ester pyridyl derivative of formula (IV);

(B)—a second step according to reaction scheme 2:

Scheme 2

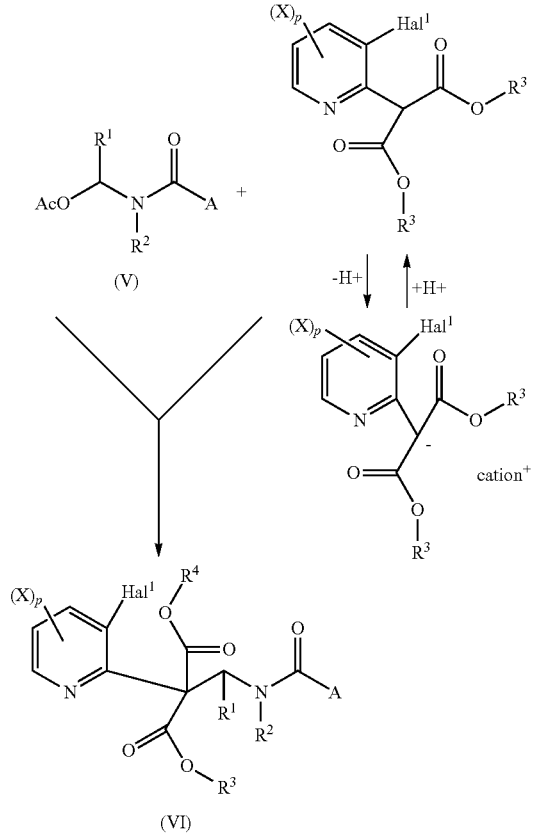

(VI)

in which:
X, $R^1$, $R^2$, $R^3$, $R^4$, $Hal^1$, X, p and A are as defined above;
Ac represents an acetyl group; and
Cation$^+$ represents Li$^+$, Na$^+$, K$^+$, Mg$^{2+}$, Ca$^{2+}$, Al$^{3+}$;
comprising the reaction of a N-acetoxymethylcarboxamide derivative of formula (V) with a malonic dialkyl ester pyridyl derivative of formula (IV) or salts thereof in a solvent to provide a 2-pyridylethylcarboxamide derivative of formula (VI);

(C)—a third step according to scheme 3:

Scheme 3

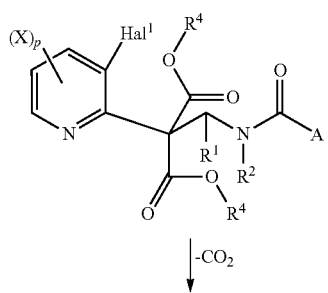

4

-continued

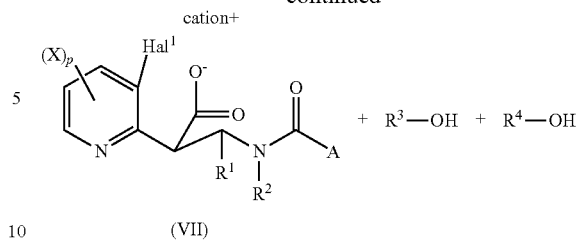

(VII)

in which:
$R^1$, $R^2$, $R^3$ and $R^4$, $Hal^1$, A, X, p are defined as above;
Cation$^+$ represents Li$^+$, Na$^+$, K$^+$, Mg$^{2+}$, Ca$^{2+}$, AL$^{3+}$;
comprising the saponification of the 2-pyridylethylcarboxamide derivative of formula (VI) obtained in step B according to scheme 2 in the presence of a base into a compound of general formula (VII)

(D)—a fourth step according to scheme 4

Scheme 4

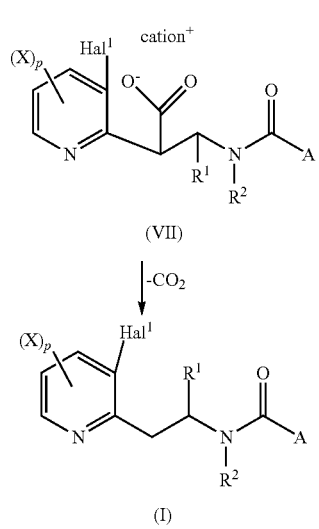

(I)

In which
$R^1$, $R^2$, $Hal^1$, A, X, p are defined as above;
Cation$^+$ represents Li$^+$, Na$^+$, K+, Mg$^{2+}$, Ca$^{2+}$, A$^{3+}$.
comprising the decarboxylation of the 2-pyridylethylcarboxamide derivative of general formula (VII) obtained in step C according to scheme 4 into a compound of general formula (I).

DETAILED DESCRIPTION OF A PREFERRED EMBODIMENT

For the purposes of the present invention:
a halogen atom may be a bromine atom, a chlorine atom, a iodine atom or a fluorine atom. Preferably, halogen atom means chlorine or fluorine atom;
carboxy means —C(═O)OH;
carbonyl means —C(═O)—;
carbamoyl means —C(═O)NH$_2$;
N-hydroxycarbamoyl means —C(═O)NHOH;
an alkyl group, an alkenyl group, and an alkynyl group as well as moieties containing these terms, can be linear or branched; and a compound used in "catalytic quantity" means that a compound is used in an amount of 0.01 to 0.2 molar equivalent, preferably from 0.01 to 0.1 molar equivalent of the respective reagent or intermediate compound.

According to the present invention, the 2-pyridyl moiety may be substituted in any position by $(X)_p$, in which X and p are as defined above. Preferably, the present invention relates to the preparation of N-[2-(2-pyridinyl)ethyl]carboxamide derivative of general formula (I) in which the different characteristics may be chosen alone or in combination as being:
- as regards p, p is 1, 2 or 3. Preferably, p is 1.
- as regards X, X is chosen, independently of the others, as being a halogen atom, a $C_1$-$C_4$-alkyl or a $C_1$-$C_4$-halogenoalkyl having 1 to 5 halogen atoms. More preferably, X is chosen, independently of the others, as being chlorine or $CF_3$;
- as regards the positions in which the 2-pyridyl moiety is substituted by X, the 2-pyridyl moiety is substituted by X in 4- and/or in 5-position. Preferably, the 2-pyridyl moiety is substituted by X in 5-position.
- $Hal^1$ may be a bromine atom, a chlorine atom, a iodine atom or a fluorine atom. Preferably, $Hal^1$ means chlorine or fluorine atom.

$Hal^2$ may be a bromine atom, a chlorine atom, a iodine atom or a fluorine atom. Preferably, $Hal^2$ means chlorine or fluorine atom.

The "ethylamide" part of the compound of formula (I) is substituted by $R^1$ and $R^2$, $R^1$ and $R^2$ being as defined above. Preferably, the present invention relates to the preparation of N-[2-(2-pyridinyl)ethyl]benzamide derivative of general formula (I) in which the different characteristics may be chosen alone or in combination as being:
- as regards $R^1$, $R^1$ is a hydrogen atom, a methyl group, $CF_3$, $CHF_2$, $CClF_2$ or $CCl_3$. More preferably, $R^1$ is a hydrogen atom;
- as regards $R^2$, $R^2$ is a hydrogen atom.

Preferably, the present invention relates to the preparation of N-[2-(2-pyridinyl)ethyl]carboxamide derivative of general formula (I) in which A is a phenyl group and in which the different characteristics may be chosen alone or in combination as being:
- A is substituted by 1 or 2 substituents. More preferably, A is substituted by 1 substituent.
- each substituent is chosen, independently of the others, as being a hydrogen atom, a halogen atom, a $C_1$-$C_4$-alkyl or a $C_1$-$C_4$-halogenoalkyl having 1 to 5 halogen atoms. More preferably each substituent is chosen, independently of the others, as being chlorine or $CF_3$;
- the phenyl moiety is substituted in ortho position.

The process of the present invention is particularly suitable for the preparation of the compound according to formula (I-a)

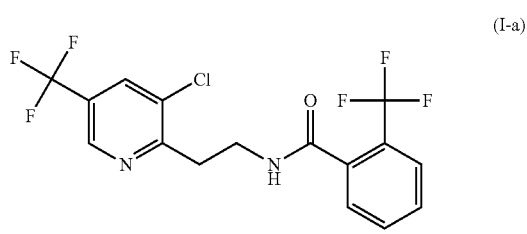 [SMILES: O=C(NCCc1ncc(C(F)(F)F)cc1Cl)c1ccccc1C(F)(F)F]

(I-a)

with the name N-{2-[3-chloro-5-(trifluoromethyl)pyridin-2-yl]ethyl}-2-(trifluoromethyl)benzamide.

The compounds according to formula (II) and (III) are commercially available.

The preparation of the compound according to formula (V) is described in WO2006/067103.

The first step (step A) of the process according to the present invention comprises the reaction of a halogenopyridyl derivative of formula (II) with a malonic dialkyl ester of formula (III) in the presence of a base and a polar solvent to provide a malonic dialkyl ester pyridyl derivative of formula (IV).

Preferably, step A may be conducted in the following conditions, chosen alone or in combination:

The ratio of the halogenopyridyl derivative of formula (II) to the malonic dialkyl ester of formula (III) may be 1:10, preferably 1:5, more preferably 1:2, most preferably between 1:1 and 1:1.2.

The malonic dialkyl ester derivative may also be present as a salt.

The solvent is chosen as being a mixture of water and of an organic solvent. Suitable organic solvent includes DMAC, NMP, or toluene or mixtures thereof.

The base is chosen as being an alkaline earth metal base, a hydroxide base, an alcoholate base, an acetate base, a carbonate base, a hydrogen carbonate base, or an organic base. Preferably, the base is chosen as being lithium hydrogen carbonate, lithium carbonate, lithium bicarbonate, lithium methanolate, lithium ethanolate, lithium acetate, lithium hydroxide, sodium hydrogen carbonate, sodium carbonate, sodium bicarbonate, sodium methanolate, sodium ethanolate, sodium acetate, sodium hydroxide, potassium hydrogen carbonate, potassium carbonate, potassium bicarbonate, potassium methanolate, potassium ethanolate, potassium acetate, potassium hydroxide, ammonium hydrogen carbonate, ammonium carbonate, ammonium bicarbonate, ammonium methanolate, ammonium ethanolate, ammonium acetate, ammonium hydroxide, magnesium hydrogen carbonate, magnesium carbonate, magnesium bicarbonate, magnesium methanolate, magnesium ethanolate, magnesium acetate, magnesium hydroxide, calcium hydrogen carbonate, calcium carbonate, calcium bicarbonate, calcium methanolate, calcium ethanolate, calcium acetate, calcium hydroxide, aluminum hydrogen carbonate, aluminum carbonate, aluminum bicarbonate, aluminum methanolate, aluminum ethanolate, aluminum acetate, aluminum hydroxide, sodium hydrogen carbonate, sodium carbonate, sodium bicarbonate, sodium methanolate, sodium ethanolate, sodium acetate, sodium hydroxide.

More preferably, the base is chosen as being sodium hydrogen carbonate, sodium carbonate, sodium bicarbonate, sodium methanolate, sodium ethanolate, sodium acetate, sodium hydroxide, potassium hydrogen carbonate, potassium carbonate, potassium bicarbonate, potassium methanolate, potassium ethanolate, potassium acetate, potassium hydroxide, magnesium hydrogen carbonate, magnesium carbonate, magnesium bicarbonate, magnesium methanolate, magnesium ethanolate, magnesium acetate, magnesium hydroxide, calcium hydrogen carbonate, calcium carbonate, calcium bicarbonate, calcium methanolate, calcium ethanolate, calcium acetate, calcium hydroxide, aluminum hydrogen carbonate, aluminum carbonate, aluminum bicarbonate, aluminum methanolate, aluminum ethanolate, aluminum acetate, aluminum hydroxide.

More preferably, the base is chosen as being sodium carbonate, sodium methanolate, sodium ethanolate, sodium acetate, sodium hydroxide, potassium carbonate, potassium methanolate, potassium ethanolate, potassium acetate, potassium hydroxide, magnesium carbonate, magnesium methanolate, magnesium ethanolate, magnesium acetate, magnesium hydroxide, calcium carbonate, calcium methanolate, calcium ethanolate, calcium acetate, calcium hydroxide, aluminum carbonate, aluminum methanolate, aluminum ethanolate, aluminum acetate, aluminum hydroxide.

Even more preferably, the base is chosen as being sodium hydroxide, sodium carbonate, potassium hydroxide, or potassium carbonate.

In one embodiment different bases can be used in combination with each other, for example sodium hydroxide and potassium hydroxide; sodium carbonate and potassium carbonate.

The temperature of step A is chosen from 0° C. to 200° C., preferably from 0° C. to 150° C., and most preferably from 0° C. to 100° C. Preferred is a temperature of 20° C. to 90° C.

Preferably the reaction of step (A) is performed under reduced pressure.

The second step (step B) of the process according to the present invention comprises the reaction of a N-acetoxymethylcarboxamide derivative of formula (V) with a malonic dialkyl ester pyridyl derivative of formula (IV) or salts thereof in a solvent to provide a 2-pyridylethylcarboxamide derivative of formula (VI).

Preferably, step B may be conducted in the following conditions, chosen alone or in combination:

The N-acetoxymethylcarboxamide derivative of formula (V) may be added to the reaction solution in situ or in solution. Alternatively the malonic dialkyl ester pyridyl derivative of formula (IV) or salts thereof in a solvent may be added to the N-acetoxymethylcarboxamide derivative of formula (V).

The solvent of step B may be the same or different than the solvent of step A.

An acid may be present in step B.

The ratio of N-acetoxymethylcarboxamide derivative of formula (V) to the malonic dialkyl ester pyridyl derivative of formula (IV) may be 10:1, preferably 5:1, more preferably 2:1 and most preferably 1:1.

The acid may be chosen as being acetic acid or formic acid.

The solvent is chosen as being an aliphatic solvent, an alicyclic solvent, an aromatic hydrocarbon solvent, a halogenated hydrocarbon solvent, an ether solvent, an amide solvent or an urea solvent. More preferably, the organic solvent is chosen as being petroleum ether, hexane, heptane, cyclo-hexane, methyl-cyclohexane, benzene, toluene, xylene, decalin, chloro-benzene, dichloro-benzene, trifluoromethyl benzene, dichloromethane, chloroform, carbon tetra-chloride, di-chloroethane, tri-chloro-ethane, diethyl ether, diisopropyl ether, methyl tert-butyl-ether, methyl tert-amyl-ether, dioxane, tetrahydrofuran, 1,2-di-methoxy-ethane, 1,2-di-ethoxy-ethane, anisole, N,N-dime-thyl-formamide, N-methyl-formanilide, N-methyl-pyrrolidone, dimethyl carbonate, diethyl carbonate, 1,3-dioxolan-2-one (Ethylene Carbonate), 4-Methyl-1,3-dioxolan-2-one (Propylene carbonate), hexamethyl-phosphoric-triamide or 1,3-dimethyl-2-2-imidazolinone or N,N-dimethyl acetamide (DMAC).

Preferred are organic solvent chosen from the group comprising N,N-dimethyl acetamide (DMAC), N-methyl-pyrrolidone, dimethyl carbonate, diethyl carbonate, 1,3-dioxolan-2-one (Ethylene Carbonate), 4-Methyl-1,3-dioxolan-2-one (Propylene carbonate).

More preferably, the organic solvent from the group comprising N-methyl-pyrrolidone or N,N-dimethyl acetamide (DMAC).

In one embodiment the solvents in step (B) can be used in mixture with other solvents, eg toluene.

The temperature of step B is chosen from 0° C. to 200° C., preferably from 0° C. to 175° C., and most preferably from 0° C. to 150° C. Preferred is a temperature between from 20° C. to 130° C.

The reaction of step B may be performed under reduced pressure.

The third step (step C) of the process according to the present invention comprises the saponification of the 2-pyridylethylcarboxamide derivative of formula (VI) obtained in step B to provide the compound according to formula (VII).

Preferably, step C may be conducted in the following conditions, chosen alone or in combination:

The ratio of 2-pyridylethylcarboxamide derivative according to formula (VI) to the base molar ratio is 1:20, preferably 1:10, more preferably 1:5 and most preferably 1:2.

The saponification may be performed in a) a two-phase system, b) an one-phase system or c) in the absence of solvent.

The two-phase system may comprise the aqueous solution of the base and the compound according to formula (VI) in an apolar solvent, the aqueous and the apolar solution being present each as one phase.

The one-phase system may comprise the base and the compound according to formula (VI) within one phase.

In one embodiment the reaction in step C may use the salt of the compound according to formula (VII) as a catalyst or emulgator.

In another embodiment the reaction in step C may convert the compound according to formula (VI) to the compound according to formula (VII) in a molten state.

The molten state refers to the compound according to formula (VI) in the absence of a solvent at a temperature above the melting point of the compound according to formula (VI).

The temperature of step C, variant a) is chosen from 0° C. to 100° C., preferably from 10° C. to 100° C., and most preferably from 10° C. to 50° C.

The temperature of step C, variant b) is chosen from 0° C. to 100° C., preferably from 10° C. to 100° C., and most preferably from 10° C. to 50° C.

The temperature of step C, variant c) is chosen from 20° C. to 150° C., preferably from 20° C. to 100° C., and most preferably from 20° C. to 80° C. In one embodiment the temperature is chosen between 40 to 100° C.

The base is chosen as being an alkaline earth metal base, a hydroxide base, an alcoholate base, an acetate base, a carbonate base, a hydrogen carbonate base, or an organic base. Preferably, the base is chosen as being lithium hydrogen carbonate, lithium carbonate, lithium bicarbonate, lithium methanolate, lithium ethanolate, lithium acetate, lithium hydroxide, sodium hydrogen carbonate, sodium carbonate, sodium bicarbonate, sodium methanolate, sodium ethanolate, sodium acetate, sodium hydroxide, potassium hydrogen carbonate, potassium carbonate, potassium bicarbonate, potassium methanolate, potassium ethanolate, potassium acetate, potassium hydroxide, ammonium hydrogen carbonate, ammonium carbonate, ammonium bicarbonate, ammonium methanolate, ammonium ethanolate, ammonium acetate, ammonium hydroxide, magnesium hydrogen carbonate, magnesium carbonate, magnesium bicarbonate, magnesium methanolate, magnesium ethanolate, magnesium acetate, magnesium hydroxide, calcium hydrogen carbonate, calcium carbonate, calcium bicarbonate, calcium methanolate, calcium ethanolate, calcium acetate, calcium hydroxide, aluminum hydrogen carbonate, aluminum carbonate, aluminum bicarbonate, aluminum methanolate, aluminum ethanolate, aluminum acetate, aluminum hydroxide, sodium hydrogen carbonate, sodium carbonate, sodium bicarbonate, sodium methanolate, sodium ethanolate, sodium acetate, sodium hydroxide.

More preferably, the base is chosen as being sodium hydrogen carbonate, sodium carbonate, sodium bicarbonate, sodium methanolate, sodium ethanolate, sodium acetate, sodium hydroxide, potassium hydrogen carbonate, potassium carbonate, potassium bicarbonate, potassium methanolate, potassium ethanolate, potassium acetate, potassium hydroxide, magnesium hydrogen carbonate, magnesium carbonate, magnesium bicarbonate, magnesium methanolate, magnesium ethanolate, magnesium acetate, magnesium hydroxide, calcium hydrogen carbonate, calcium carbonate, calcium bicarbonate, calcium methanolate, calcium ethanolate, calcium acetate, calcium hydroxide, aluminum hydrogen carbonate, aluminum carbonate, aluminum bicarbonate, aluminum methanolate, aluminum ethanolate, aluminum acetate, aluminum hydroxide.

More preferably, the base is chosen as being sodium carbonate, sodium methanolate, sodium ethanolate, sodium acetate, sodium hydroxide, potassium carbonate, potassium methanolate, potassium ethanolate, potassium acetate, potassium hydroxide, magnesium carbonate, magnesium methanolate, magnesium ethanolate, magnesium acetate, magnesium hydroxide, calcium carbonate, calcium methanolate, calcium ethanolate, calcium acetate, calcium hydroxide, aluminum carbonate, aluminum methanolate, aluminum ethanolate, aluminum acetate, aluminum hydroxide.

Even more preferably, the base is chosen as being sodium hydroxide, sodium carbonate, potassium hydroxide, potassium carbonate, magnesium hydroxide, or calcium hydroxide.

In one embodiment mixtures of bases may be used.

In one embodiment different bases can be used in combination with each other, for example sodium hydroxide and potassium hydroxide; sodium carbonate and potassium carbonate.

The organic solvent is chosen as being an aliphatic solvent, an alicyclic solvent, an aromatic hydrocarbon solvent, a halogenated hydrocarbon solvent, an ether solvent, an amide solvent, nitrile solvents, alcohols, water or an urea solvent.

More preferably, the organic solvent is chosen as being petroleum ether, hexane, heptane, cyclo-hexane, methylcyclohexane, benzene, toluene, xylene, decalin, chloro-benzene, dichloro-benzene, trifluoromethyl benzene, dichloromethane, chloroform, carbon tetra-chloride, di-chlorethane, tri-chlor-ethane, diethyl ether, diisopropyl ether, methyl tert-butyl-ether, methyl tert-amyl-ether, cyclopentyl-methyl-ether, dioxane, tetrahydrofuran, methyl tetrahydrofuran, 1,2-di-methoxyethane, 1,2-di-ethoxy-ethane, anisole, N,N-dimethyl-formamide, N,N-dimethyl-acetamide, N-methyl-formanilide, acetonitrile, butyronitrile, methanol, ethanol, isopropanol, 1-propanol, 2-methoxy ethanol, tert. butanol, 1-butanol, 2-butanol, cyclohexanol, ethandiole, ethylene glycol, N-methyl-pyrrolidone, hexamethyl-phosphoric-triamide or 1,3-dimethyl-2-2-imidazolinone or N,N-dimethyl acetamide (DMAC).

Even more preferably, the organic solvent is chosen as being tetrahydrofuran (THF) or N,N-dimethyl acetamide (DMAC).

The fourth step (step D) of the process according to the present invention comprises the decarboxylation of the 2-pyridylethylcarboxamide derivative obtained in step C into a compound of general formula (I) as defined above. Such a decarboxylation reaction may be performed by known methods. Such a decarboxylation reaction may for example be conducted according to the Krapcho reaction described in A.P. *Synthesis,* 1982, 805, 893, herein incorporated by reference.

The compound of general formula (I) according to the present invention can be prepared according to the above described process. It will nevertheless be understood that, on the basis of his general knowledge and of available publications, the skilled worker will be able to adapt this method according to the specifics of each of the compounds, which it is desired to synthesise.

The present invention will now be illustrated with reference to the following examples.

Preparation of N-{2-[3-chloro-5-(trifluoromethyl)-2-pyridinyl]ethyl}-2-trifluoromethylbenzamide Step A Synthesis of dimethyl [3-chloro-5-(trifluoromethyl) pyridin-2-yl]malonate Potassium hydroxide was mixed with the solvent dimethylacetamide at room temperature and heated at 62 degree Celsius.

Dimethylmalonate and 2,3-dichloro-5-(trifluoromethyl) pyridine of formula (II-a)

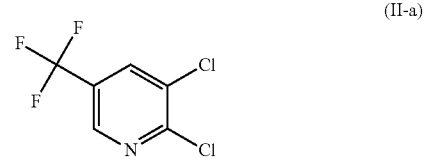 [SMILES: FC(F)(F)c1cnc(Cl)c(Cl)c1]

(II-a)

in a 1:1 molar ratio were added to the dimethylacetamide/ KOH mixture until a precipitate of the product dimethyl [3-chloro-5-(trifluoromethyl)pyridin-2-yl]malonate of formula (IV-a)

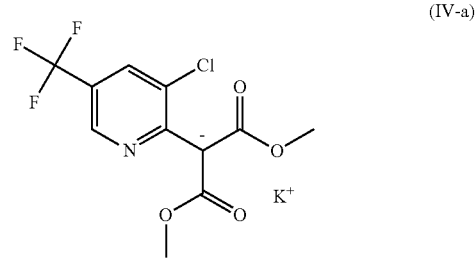 [SMILES: COC(=O)[C-](C(=O)OC)c1ncc(C(F)(F)F)cc1Cl ; [K+]]

(IV-a)

is formed.

The conversion and the formation of the product according to formula (IV-a) was analyzed using HPLC.

Step B: Synthesis of Dimethyl [2-(benzoylamino)ethyl][3-chloro-5-(trifluoromethyl)pyridin-2-yl]malonate Acetic acid was added to a suspension of dimethyl [3-chloro-5-(trifluoromethyl)pyridin-2-yl]malonate of formula (IV-a) of step (A) at a temperature of 60 degree Celsius.

{[2-(trifluoromethyl)benzoyl]amino}methyl acetate of formula (V-a)

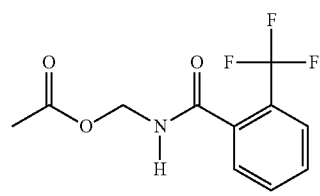
(V-a)

was added to the suspension, further incubated and the temperature raised to 80 degrees Celsius. The solvent DMAC was removed by distillation. The residue, consisting mainly of dimethyl [2-(benzoylamino)ethyl][3-chloro-5-(trifluoromethyl)pyridin-2-yl]malonate of formula (VI-a)

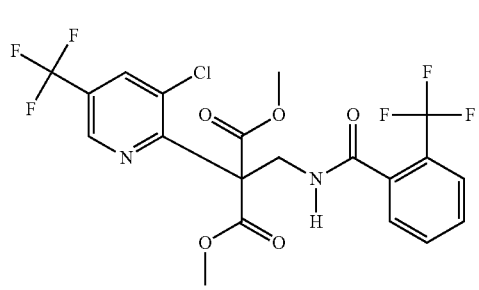
(VI-a)

and inorganic salts, was dissolved in water and methyl tert-butyl ether (MTBE). After phase separation the water phase comprising inorganic salts was discharged and the MTBE phase containing the product is used in step (C).

Step (C): Saponification of dimethyl [2-(benzoylamino)ethyl][3-chloro-5-(trifluoromethyl)pyridin-2-yl]malonate of formula (VI-a)

If necessary, additional water was added to the MTBE phase dimethyl [2-(benzoylamino)ethyl][3-chloro-5-(trifluoromethyl)pyridin-2-yl]malonate of formula (VI-a). In order to perform the saponification sodium hydroxide at a ratio of 3.5 to 1 to the dimethyl [2-(benzoylamino)ethyl][3-chloro-5-(trifluoromethyl)pyridin-2-yl]malonate of formula (VI-a) was added to the MTBE phase and stirred for several hours, thereby generating the product.

The rate of formation of sodium 2-[3-chloro-5-(trifluoromethyl)pyridin-2-yl]-3-{[2 (trifluoromethyl)benzoyl]amino}propanoate according to formula (VII-a)

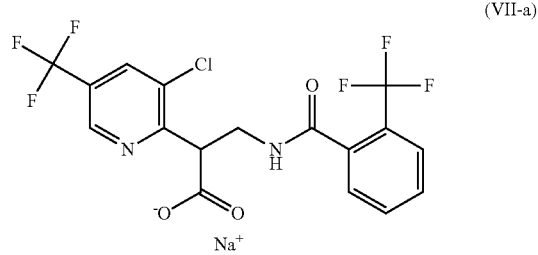
(VII-a)

was monitored.

2-[3-chloro-5-(trifluoromethyl)pyridin-2-yl]-3-{[2 (trifluoromethyl)benzoyl]amino}propanoate, here as the sodium salt can be used as a catalyst in the saponification process.

For additional amounts of the product of step (B) as MTBE solution together with additional sodium hydroxide and water are added to the reaction mixture comprising the compound according to formula (VII-a) at 35 degree Celsius. Water is added to dissolve the sodium salt of compound (VII-a), the MTBE is removed by distillation under reduced pressure.

Step D: Synthesis of N-{2-[3-chloro-5-(trifluoromethyl)pyridin-2-yl]ethyl}-2-(trifluoromethyl)benzamide of formula (I-a)

Methanol is added to the reaction mixture of step (C) followed by the addition of hydrochloric acid until a pH of lower than 3 is achieved. The product N-{2-[3-chloro-5-(trifluoromethyl)pyridin-2-yl]ethyl}-2-(trifluoromethyl)benzamide according to formula (I-a)

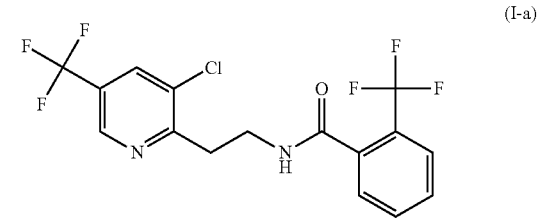 [SMILES: O=C(NCCc1ncc(C(F)(F)F)cc1Cl)c1ccccc1C(F)(F)F]
(I-a)

was precipitated. The temperature was lowered below 20 degrees and continuously stirred. The precipitate was washed several times with a mixture of methanol and water and was finally dried. The product was analyzed using HPLC. A purity of 98.4% was achieved; the overall yield was 86.56%.

The invention claimed is:

1. A process for preparation of a N-[2-(2-pyridinyl)ethyl] carboxamide derivative of formula (I) or a salt thereof

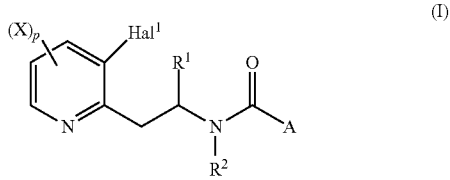
(I)

in which:

p is an integer equal to 1, 2, or 3;

X is the same or different and is a hydrogen atom, a halogen atom, a $C_1$-$C_8$-alkyl, or a $C_1$-$C_8$-halogenoalkyl having 1 to 5 halogen atoms;

$Hal^1$ represents a halogen atom;

$R^1$ is a hydrogen atom, a $C_1$-$C_8$-alkyl, a $C_1$-$C_8$-halogenoalkyl having 1 to 5 halogen atoms or a $C_1$-$C_8$-alkoxycarbonyl;

$R^2$ is a hydrogen atom or a cyclopropyl group; and

A represents a phenyl group optionally substituted by one or more substituents independently selected from the group consisting of a halogen atom, a $C_1$-$C_8$-alkyl, and a $C_1$-$C_8$-halogenoalkyl having 1 to 5 halogen atoms;

said process comprising:

(A) reacting a halogenopyridyl derivative of formula (II) with a malonic dialkyl ester of formula (III) in the presence of a base and a polar solvent to produce a malonic dialkyl ester pyridyl derivative of formula (IV)

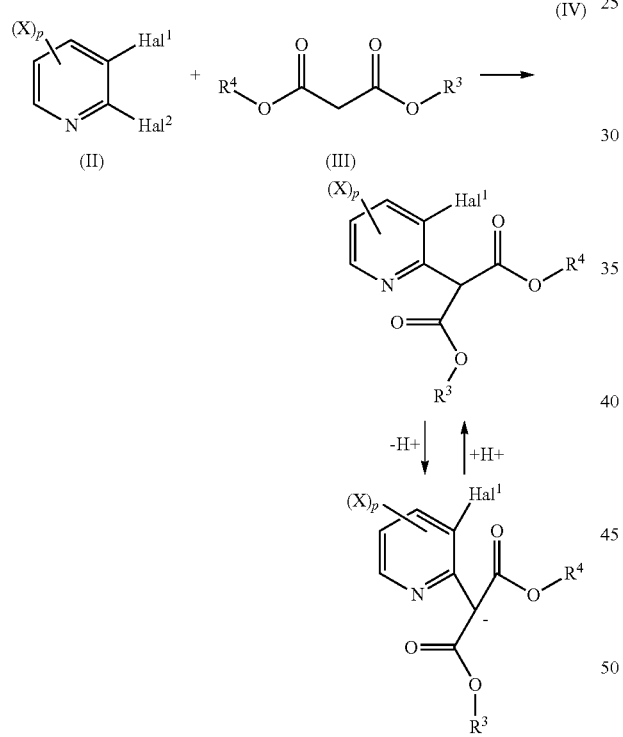

in which:

A and $R^2$ are as defined above;

X and p are defined as above; and $Hal^1$ or $Hal^2$ represent independently from each other a halogen atom;

$R^3$ and $R^4$ represent independently from each other a $C_1$-$C_6$-alkyl;

(B) reacting a N-acetoxymethylcarboxamide derivative of formula (V) with a malonic dialkyl ester pyridyl derivative of formula (IV) or salts thereof in a solvent to produce a 2-pyridylethylcarboxamide derivative of formula (VI)

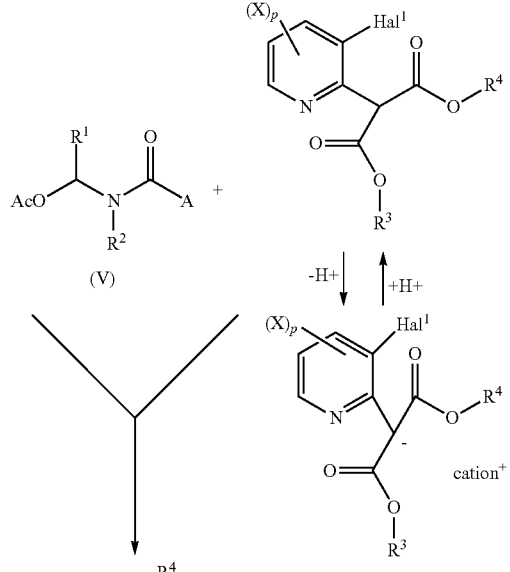

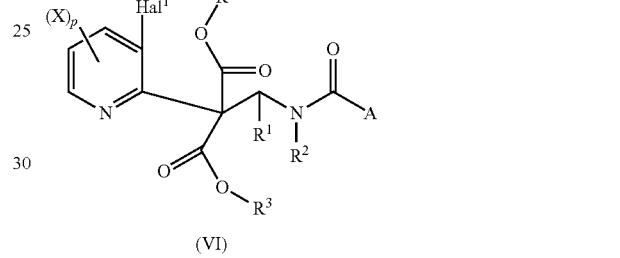

in which:

X, $R^1$, $R^2$, $R^3$, $R^4$, $Hal^1$, p and A are as defined above;

Ac represents an acetyl group; and $cation^+$ represents a stoichiometric amount of $Li^+$, $Na^+$, $K^+$, $Mg^{2+}$, $Ca^{2+}$, or $Al^{3+}$;

(C) saponification of the 2-pyridylethylcarboxamide derivative of formula (VI) obtained in B in the presence of a base into a compound of formula (VII)

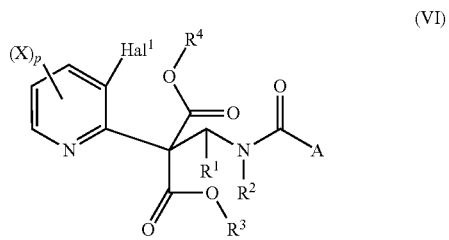

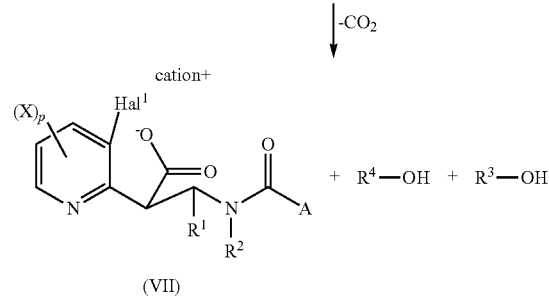

in which:
$R^1$, $R^2$, $R^3$ and $R^4$, $Hal^1$, A, X, p are defined as above;
cation$^+$ represents a stoichiometric amount of Li$^+$, Na$^+$, K$^+$, Mg$^{2+}$, Ca$^{2+}$, or Al$^{3+}$; and
(D) decarboxylation of the 2-pyridylethylcarboxamide derivative of formula (VII) obtained in C into a compound of formula (I)

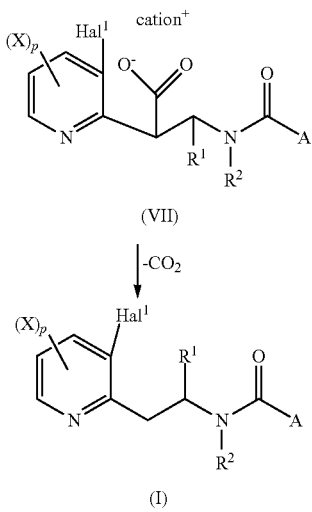

in which
$R^1$, $R^2$, $Hal^1$, A, X, p are defined as above; and
cation$^+$ represents a stoichiometric amount of Li$^+$, Na$^+$, K$^+$, Mg$^{2+}$, Ca$^{2+}$, or Al$^{3+}$.

2. The process according to claim 1, wherein p is 1.

3. The process according to claim 1 wherein X is chosen, independently of the others, as being chlorine or CF$_3$.

4. The process according to claim 1, wherein the 2-pyridyl moiety is substituted by X in 5-position.

5. The process according to claim 1, wherein R' is a hydrogen atom, a methyl group, CF$_3$, CHF$_2$, CClF$_2$ or CCl$_3$.

6. The process according to claim 1, wherein R$^2$ is a hydrogen atom.

7. The process according to claim 1, wherein A is a phenyl group.

8. The process according to claim 7, wherein A is substituted by one or two substituents, the substituent of A is chosen, independently of each other, as being chlorine or CF$_3$.

9. The process according claim 7, wherein the A is substituted in ortho position.

10. The process according to claim 1, wherein the compound of formula (I) is:
N-{2-[3-chloro-5-(trifluoromethyl)-2-pyridinyl]ethyl}-2-trifluoromethylbenzamide.

11. The process according to claim 1, wherein A is conducted in the presence of an organic solvent or a mixture thereof.

12. The process according to claim 1, wherein A is conducted at reduced pressure.

13. The process according to claim 1, wherein C is conducted in a two-phase system in the absence of solvent.

14. The process according to claim 1, wherein C is conducted in a one-phase system.

15. The process according to claim 1, wherein C is conducted in the absence of solvent in a molten state.

* * * * *